(12) United States Patent
Fenchel et al.

(10) Patent No.: US 8,618,490 B2
(45) Date of Patent: Dec. 31, 2013

(54) METHOD FOR DETERMINING RADIATION ATTENUATION IN A POSITRON EMISSION TOMOGRAPHY SCANNER

(75) Inventors: Matthias Fenchel, Erlangen (DE); Ralf Ladebeck, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 286 days.

(21) Appl. No.: 13/160,616

(22) Filed: Jun. 15, 2011

(65) Prior Publication Data

US 2011/0309251 A1 Dec. 22, 2011

(30) Foreign Application Priority Data

Jun. 17, 2010 (DE) .......................... 10 2010 024 139

(51) Int. Cl.
*G01T 1/166* (2006.01)
*A61B 5/05* (2006.01)

(52) U.S. Cl.
USPC ............. 250/363.04; 250/260; 250/252.1; 250/363.02; 250/363.03; 250/395; 600/407

(58) Field of Classification Search
USPC ............... 250/363.03–363.04, 252.1, 260; 600/407
See application file for complete search history.

(56) References Cited

U.S. PATENT DOCUMENTS

| | | | |
|---|---|---|---|
| 7,923,691 B2 | 4/2011 | Ladebeck | |
| 2009/0278049 A1 * | 11/2009 | Ladebeck | 250/361 R |
| 2010/0135559 A1 * | 6/2010 | Morich et al. | 382/131 |

FOREIGN PATENT DOCUMENTS

| | | |
|---|---|---|
| DE | 102008022816 A1 | 11/2009 |
| WO | WO 2008135873 A1 * | 11/2008 |

OTHER PUBLICATIONS

Bin Zhang at al.: "Attenuation correction for MR table and coils for a sequential PET/MR system", 2009 IEEE Nuclear Science Symposium Conference Record, M09-245, p. 3303-3306; Others; 2009.
Hoffmann at al.: "Towards quantitative PET/MRI: a review of MR-based attenuation correction techniques", Eur. J. Nucl. Med. Mol. Imaging (2009), 36, p. S94-104, Springer; Others; 2009.
Gaspar Delso at al.: "Study of MR head and neck coils for its use in an integrated MR/PET scanner", J. Nucl. Med. Meeting Abstracts 2009 50:1476; Others; 2009.
German priority application DE 10 2010 024 139.3 filed on Jun. 17, 2010 and not yet published.

\* cited by examiner

*Primary Examiner* — David Porta
*Assistant Examiner* — Jeremy S Valentiner
(74) *Attorney, Agent, or Firm* — Harness, Dickey & Pierce, P.L.C.

(57) ABSTRACT

A method is disclosed for determining radiation attenuation as a result of an object in a positron emission tomography scanner. In at least one embodiment, a phantom object is arranged in the positron emission tomography scanner during the method. First raw radiation data of the phantom object is acquired while the object is not arranged in the positron emission tomography scanner. A first image of the phantom object is calculated from the first raw radiation data. The object then is arranged in the positron emission tomography scanner (2) and preliminary radiation attenuation of the object is identified. Second raw radiation data of the phantom object is acquired while the object is arranged in the positron emission tomography scanner. A second image of the phantom object is calculated from the second raw radiation data taking into account the preliminary radiation attenuation. The radiation attenuation is determined on the basis of the first image and the second image.

19 Claims, 2 Drawing Sheets

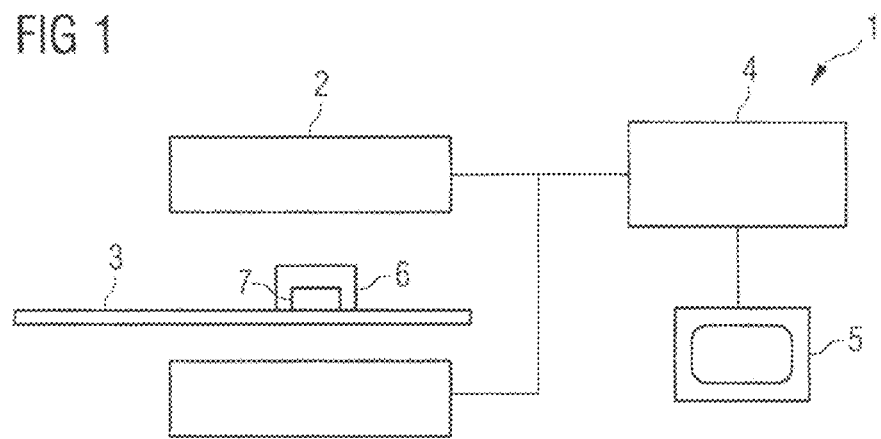
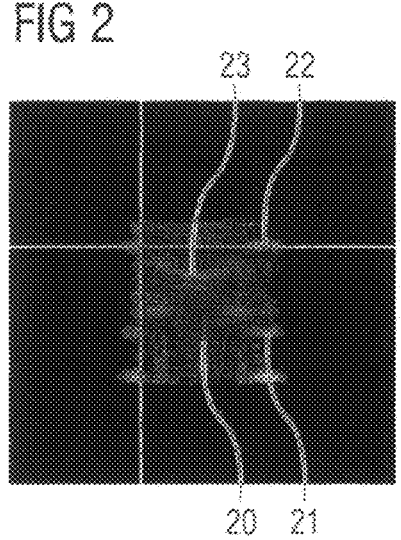
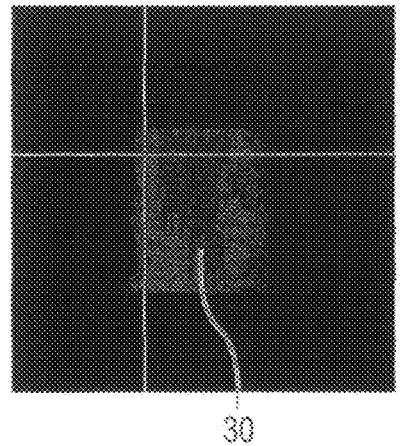

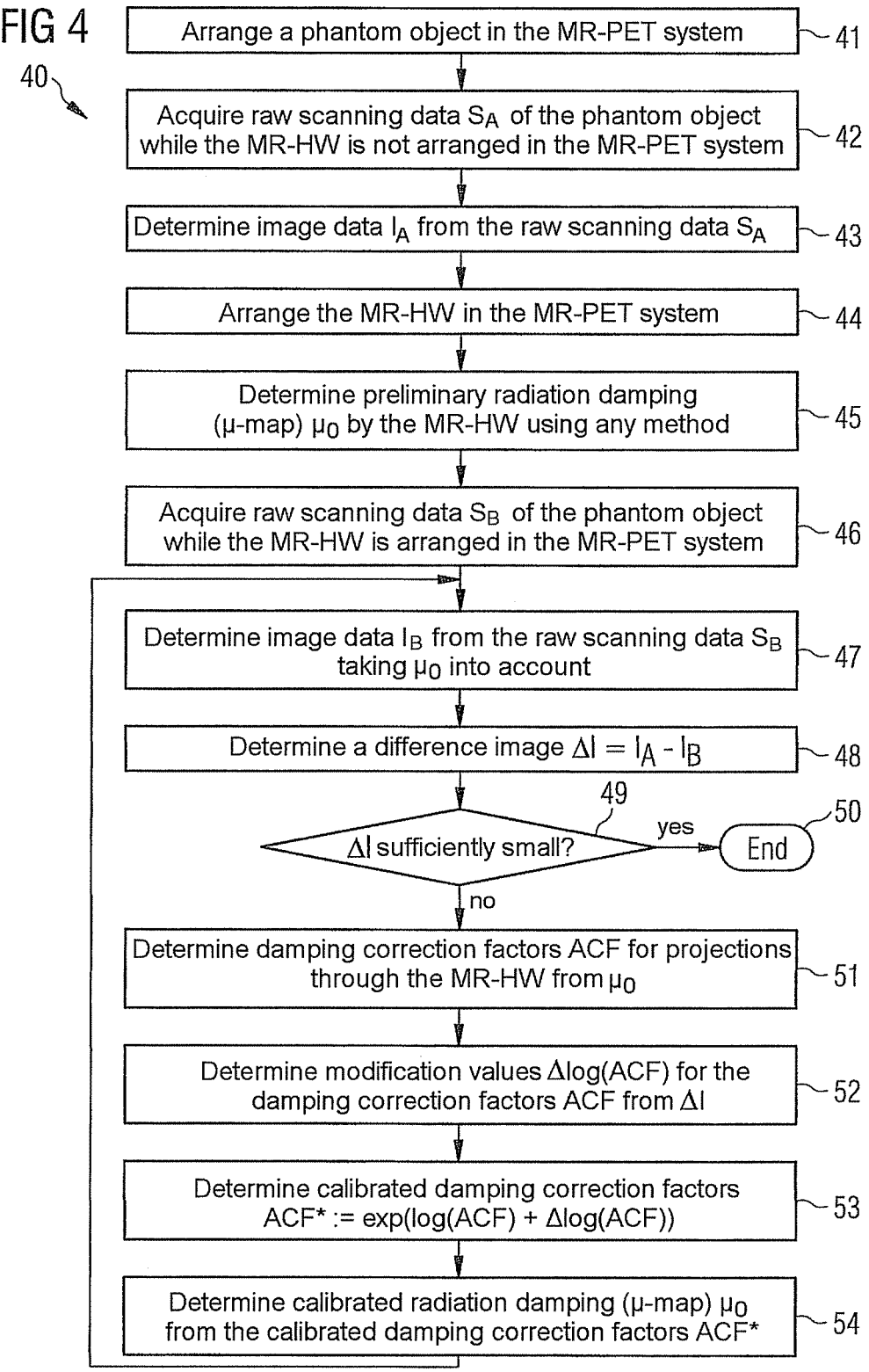

ately relates to a method for determining radiation attenuation as a result of an object in a positron emission tomography scanner and/or to a device for a positron emission tomography system for determining radiation attenuation as a result of an object in a positron emission tomography scanner of the positron emission tomography system.

METHOD FOR DETERMINING RADIATION ATTENUATION IN A POSITRON EMISSION TOMOGRAPHY SCANNER

PRIORITY STATEMENT

The present application hereby claims priority under 35 U.S.C. §119 on German patent application number DE 10 2010 024 139.3 filed Jun. 17, 2010, the entire contents of which are hereby incorporated herein by reference.

FIELD

At least one embodiment of the present invention generally relates to a method for determining radiation attenuation as a result of an object in a positron emission tomography scanner and/or to a device for a positron emission tomography system for determining radiation attenuation as a result of an object in a positron emission tomography scanner of the positron emission tomography system.

BACKGROUND

In order to determine an attenuation correction in a positron emission tomography (PET) scanner, use can be made of a combination of a magnetic resonance system and a positron emission tomography system, a so-called MR-PET hybrid system. However, a problem in using such MR-PET hybrid systems is the fact that local coils, which are used to receive the magnetic resonance signals from the examination object (for example, a human body), are not visible in conventional clinical magnetic-resonance scanning techniques. However, these coils can have a significant influence on the emission data of the positron emission tomography scanner, and so the attenuation thereof must be corrected in order to obtain artifact-free and quantitative PET images.

The prior art has proposed various approaches to measure the attenuation of these objects, i.e. the local coils, or to determine the attenuation thereof directly.

By way of example, in "Towards quantitative PET/MRI: A review of MR-based attenuation correction techniques" by M. Hofmann, B. Pichler, B. Schölkopf, and T. Beyer (European Journal of Nuclear Medicine and Molecular Imaging 36 (Supplement 1), 93-104 (03 2009)), the entire contents of which are hereby incorporated herein by reference, it is proposed to scan the objects in a CT scanner and to transfer the measured transmission values to the attenuation at 511 keV. However, the CT images of the object may contain metallic artifacts. Furthermore, partial volume effects may occur and the transformation of the linear attenuation coefficients for non-tissue material to 511 keV is complicated.

In "Study of MR head and neck coils for its use in an integrated MR/PET-scanner" by Gaspar Delso, Alex Martinez, Ralph Bundschuh, Ralf Ladebeck, David Faul, and Sibylle Ziegler (J. Nucl. Med. Meeting Abstracts 2009 50:1476) and in "Attenuation Correction for MR Table and Coils for a Sequential PET/MR System" by Bin Zhang, Debashish Pal, Zhigiang Hu, Navaeep Ojha, Tiantui Guo, Gary Muswick, Chi-Hua Tung, and Jeff Kaste (IEEE MIC, 2009), the entire contents of each of which are hereby incorporated herein by reference, it is proposed to scan the objects in a PET system with an emission source. However, this acquisition takes a very long time, the resulting image is very rough, and it is not possible to distinguish between small structures.

Finally, there is the option of determining the attenuation images from design drawings by converting CAD structures into volume images, wherein the individual voxels in the volume images are provided with the physical linear attenuation coefficients. However, in general, not all parts are available as a model. Often it is only the plastic parts that are available as a model. Other parts, such as e.g. metal parts, can therefore only be modeled in a generic fashion, as a result of which the actual local structure of the linear attenuation coefficients can only be derived imprecisely and with great difficulty. Moreover, each coil can slightly deviate from the determined attenuation image as a result of production tolerances.

SUMMARY

In at least one embodiment of the present invention, an improved method is provided for determining radiation attenuation of objects, such as e.g. local coils, in a positron emission tomography scanner.

A method is disclosed, in at least one embodiment, for determining radiation attenuation as a result of an object in a positron emission tomography scanner; a device is disclosed, in at least one embodiment, for a positron emission tomography system; an MR-PET hybrid system is disclosed, in at least one embodiment; a computer program product is disclosed, in at least one embodiment; and an electronically readable data medium is disclosed, in at least one embodiment. The dependent claims define preferred and advantageous embodiments of the invention.

According to at least one embodiment of the present invention, provision is made for a method for determining radiation attenuation as a result of an object in a positron emission tomography scanner. Within the scope of at least one embodiment of the method, a test object, a so-called phantom object, is firstly arranged in the positron emission tomography scanner. The phantom object is an object with a defined size and shape, which has a positron emission source, that is to say it is an object that emits high-energy photons in a defined fashion as a result of an interaction within the phantom object between a positron and an electron.

In a further step of the method, first raw radiation data of the phantom object is automatically acquired with the aid of the positron emission tomography scanner, wherein the object (also referred to as non-phantom object), whose radiation attenuation should be determined by the method is not situated in the positron emission tomography scanner during this acquisition of the first raw radiation data. By way of example, the object can comprise one or more local coils for a magnetic resonance examination. A first attenuation-corrected PET image of the phantom object is automatically calculated on the basis of the first raw radiation data. Methods for calculating attenuation-corrected tomographic PET images are known to a person skilled in the art and are not explained in any more detail. The object, that is to say, for example, a local coil of a magnetic resonance system, is then arranged in the positron emission tomography scanner.

Preliminary radiation attenuation of the object arranged in the positron emission tomography scanner is determined or identified with the aid of methods known from the prior art, as described above in the introduction, the entire contents of each of which are hereby incorporated herein by reference. As described above, this determination or identification can be carried out for example by scanning the object in a computed tomography scanner and converting measured transmission values to attenuation at 511 keV, by scanning the object in the positron emission tomography scanner with an emission source, or by determining the preliminary radiation attenuation from a geometry, dimensions, and physical attenuation coefficients of the object. The preliminary radiation attenuation can be identified relatively imprecisely because it is determined precisely with the aid of the method according to the invention.

While the object is arranged in the positron emission tomography scanner, second raw radiation data of the phantom object is then acquired automatically with the aid of the positron emission tomography scanner in a further step of the method. A second attenuation-corrected PET image of the phantom object is calculated automatically from the second raw radiation data, taking into account the previously identified preliminary radiation attenuation. Finally, the radiation attenuation is then calibrated automatically on the basis of the first image and the second image, that is to say the preliminary radiation attenuation is improved on the basis of the first image and the second image such that more precise radiation attenuation of the object is determined.

Rather than directly determining the radiation attenuation of the object, such as e.g. the local coils, in a positron emission tomography scanner, as is conventional in the prior art, the method according to at least one embodiment of the invention uses preliminary or initial radiation attenuation, which may contain errors, and this radiation attenuation is calibrated, and hence improved, with the aid of images of the test or phantom object without the object and with the object. The calibration procedure can also be carried out repeatedly in an iterative fashion, wherein the calibrated radiation attenuation is used as preliminary radiation attenuation in the subsequent iteration step.

Since the raw radiation data does not change between the individual iteration steps, an iteration merely comprises the calculation of the second image taking into account the preliminary radiation attenuation (or the more precise radiation attenuation determined up until that point) and the calibration of the radiation attenuation on the basis of the first and the second image. Hence, the iterations can be carried out automatically by a corresponding computer system until, for example, a difference image between the first image and the second image only still has deviations below a prescribed threshold. Other abort criteria are also possible, for example a predetermined maximum number of iterations or a minimal change between the radiation attenuation in the last iteration and the radiation attenuation in the current iteration.

Hence, by calibrating the radiation attenuation according to the above-described method, the second image of the phantom object, which was acquired while the object is arranged in the positron emission tomography scanner, is adjusted to the first image, which was acquired while the object is not arranged in the positron emission tomography scanner. This affords the possibility of determining very precise radiation attenuation of the object, and there is no need to optimize the object, e.g. local coils, for use in a hybrid MR-PET system.

According to one embodiment of the method, the step of calibrating the radiation attenuation comprises the following steps: a difference image is firstly determined automatically from the first image and the second image. By way of example, this can be carried out by forming a difference value for each pixel. Attenuation correction factors for (forward) projections through the object are determined on the basis of the preliminary radiation attenuation or, in the case of the above-described iteration, on the basis of the radiation attenuation from the last iterative step. By way of example, this determination can be carried out with the aid of a so-called Radon transform. Furthermore, modification values for the attenuation correction factors are determined on the basis of the difference image. The attenuation correction factors are then corrected on the basis of these modification values and the calibrated radiation attenuation is finally determined on the basis of the modified attenuation correction factors, for example with the aid of the inverse Radon transform.

In this context, the terms radiation attenuation and attenuation correction factor are explained in more detail below. The term radiation attenuation, as used in the present invention, relates to an attenuation value that is assigned to a voxel of the object. The totality of the radiation attenuation with its spatial assignment is also referred to as a μ-map. The term attenuation correction factor, as used in at least one embodiment of the present invention, refers to attenuation along a straight projection line through the object. The radiation attenuation can be converted into attenuation correction factors, and vice versa, with the aid of for example the Radon transform (forward projection) and the inverse Radon transform (back projection). Instead of a simple back projection, use is often made of a so-called filtered back projection, which undoes a convolution of the back-projected image. These methods are known to a person skilled in the art and are not described in any more detail.

As will be demonstrated below, converting the radiation attenuation into attenuation correction factors and correcting the attenuation correction factors on the basis of modification values emerging from the difference image is advantageous because modifying the attenuation correction factors can be reduced to a simple addition of logarithmized values.

Hence, according to one embodiment, logarithmic modification values are determined for the attenuation correction factors for the projections through the object by forward projection of the difference image. The logarithmic modification values are then added to form logarithmized attenuation correction factors, which were determined for projections through the object on the basis of the preliminary radiation attenuation. Finally, the corrected or calibrated radiation attenuation is determined by back projection from the modified logarithmized attenuation correction factors. Hence, the method defined thus can easily be carried out in an automated fashion by a corresponding computer system.

According to at least one embodiment of the present invention, provision is furthermore made for a device for a positron emission tomography system for determining radiation attenuation as a result of an object in a positron emission tomography scanner of the positron emission tomography system. The device comprises a control unit for actuating a positron emission detector of the positron emission tomography scanner and an image-calculation unit for receiving raw radiation data acquired by the positron emission detector and for reconstructing image data from the raw radiation data. The device is embodied to acquire first raw radiation data of a phantom object arranged in the positron emission tomography scanner, while the object is not arranged in the positron emission tomography scanner. The phantom object has a positron emission source and is able to emit high-energy photons as a result of an interaction between a positron and an electron. In the process, it is advantageous if the geometry of the phantom object is such that all lines of response, which should be corrected in subsequent patient scans, are already covered by the phantom.

The device is furthermore embodied to calculate a first image of the phantom object from the first raw radiation data. Furthermore, the device is able to process initial radiation attenuation or preliminary radiation attenuation (a so-called initial μ-map) of the object, which is arranged in the positron emission tomography scanner, with the aid of methods known from the prior art, as described in the introduction and incorporated herein by reference, (the initial μ-map can originate from any other system), and the device is also able to adjust the position of the object, given in the μ-map to be processed, to the physical position of the object in the device. Moreover, the device is able to acquire second raw radiation data of the phantom object while the object is arranged in the positron emission tomography scanner and to calculate a second image of the phantom object from the second raw radiation data taking into account the preliminary radiation attenuation. Finally, the device is embodied such that it calibrates the radiation attenuation on the basis of the first and the second image. By way of example, the positron emission tomography system can be a combined magnetic resonance and positron emission tomography system, a so-called MR-PET hybrid system, wherein the object comprises one or more local coils of the magnetic resonance system.

According to one embodiment, the device is embodied such that it can carry out the above-described method or one of its embodiments.

According to at least one embodiment of the present invention, provision is furthermore made for a MR-PET hybrid system with the above-described device. Hence, the MR-PET hybrid system likewise comprises the advantages of the above-described device and of the above-described method.

At least one embodiment of the present invention furthermore comprises a computer program product, more particularly software, which can be loaded into a storage medium of a programmable control unit of a device for a positron emission tomography system. When the computer program product is executed in the magnetic resonance system, all the above-described embodiments of the method according to at least one embodiment of the invention can be executed using program means of this computer program product.

Finally, at least one embodiment of the present invention provides an electronically readable data medium, e.g. a CD or a DVD, on which electronically readable control information, more particularly software, is stored. When this control information is read by the data medium and stored in a control unit of a device for a positron emission tomography system, all embodiments according to the invention of the above-described method can be carried out using the positron emission tomography system.

BRIEF DESCRIPTION OF THE DRAWINGS

In the following text, the present invention is explained on the basis of example embodiments, with reference being made to the drawings.

FIG. 1 shows a schematic view of an MR-PET hybrid system as per an embodiment of the present invention.

FIG. 2 shows a positron emission tomography recording of a phantom object, which was determined with the aid of preliminary radiation attenuation.

FIG. 3 shows a positron emission tomography recording of the phantom object, which was determined with radiation attenuation calibrated according to an embodiment of the present invention.

FIG. 4 shows a flowchart of an embodiment of the method according to an embodiment of the invention for determining radiation attenuation as a result of an object in a positron emission tomography scanner.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments.

The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood, that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a MR-PET hybrid system 1, which comprises a combined magnetic resonance-positron emission tomography scanner 2 (MR-PET tomography scanner), an examination table 3 arranged within the MR-PET tomography scanner, a control unit 4, and an image-calculation unit 5. The control unit 4 is embodied to actuate the MR-PET hybrid tomography scanner 2, and the examination table 3 arranged therein, in order to acquire positron emission tomography recordings and magnetic resonance recordings from an examination object or patient arranged on the examination table 3 and, with the aid of the image-calculation unit 5, to image said examination object or patient on a monitor of the image-calculation unit 5. The general method of operation of the tomography scanner 2, the control unit 4 and the image-calculation unit 5 is known to a person skilled in the art and therefore it is not explained in any more detail here.

The image quality of a positron emission tomography recording can be improved significantly by using a MR-PET hybrid system. However, a magnetic-resonance-based attenuation correction of the radiation data is made more difficult in MR-PET hybrid systems by virtue of the fact that local coils, which are used to receive the magnetic-resonance signal from the patient, are not visible in conventional magnetic-resonance scanning techniques. However, these coils can have a significant influence on the radiation data in the positron emission tomography recordings, and hence the attenuation of said coils must be corrected in order to avoid artifacts and obtain quantitative PET recordings. To this end, the radiation attenuation of the local coils should be determined as precisely as possible. In the following text, this radiation attenuation is also referred to as a μ-map.

Hence, according to the embodiment of the present invention described here, an iterative method is carried out in the control unit 4 and the image-calculation unit 5, in which method, starting from a relatively imprecise image of the radiation attenuation or μ-map of the local coils, an improved μ-map is provided by adding attenuation to regions that were previously under-corrected and by removing attenuation in regions that were previously over-corrected. With reference to FIG. 4, the method is described below in the form of a scheduling method 40.

In step 41 of the method 40, a test object 6, a so-called phantom object, is arranged in the MR-PET system 1. By way of example, the phantom object 6 can be arranged on the object table 3 within the tomography scanner 2. The phantom object 6 has a positron emission source, as a result of which high-energy photon pairs are created in the phantom object 6 by the combination of positrons and electrons, which high-energy photon pairs can be acquired by the positron emission tomography scanner 2 and can be used to generate positron emission tomography recordings. Accordingly, raw scanning data SA of the phantom object 6 is acquired in step 42 with the aid of the positron emission tomography scanner 2. Local coils (as an example of magnetic resonance hardware MR-HW), which can be used in MR-PET hybrid systems, are not arranged within the tomography scanner 2 at this time. Image data IA of the phantom object 6 is determined in step 43 from the raw scanning data SA with the aid of the image-calculation unit 5. FIG. 3 shows an image 30 of the phantom object 6, which image corresponds to the image data IA.

In addition to the phantom object 6, one or more local coils 7 are arranged on the object table 3 in the tomography scanner 2 in step 44. The local coils 7 are advantageously arranged such that they are in the same position within the MR-PET system as during later use in conjunction with a patient. As per known methods as described in the introduction, preliminary radiation attenuation or a μ-map of the local coils is determined in step 45. This preliminary μ-map can be relatively imprecise. By way of example, this preliminary μ-map may be determined approximately from the geometric structures of the local coils. Raw scanning data $S_B$ of the phantom object is then acquired in step 46 while the local coils 7 are arranged in the MR-PET system 1. Image data $I_B$ of the phantom object 6 is then determined in step 47 from the raw scanning data $S_B$ whilst using the preliminary μ-map. FIG. 2 shows a possible result from this image data $I_B$. An image 20 of the phantom object 6 can be identified in FIG. 2, in which the interior of the phantom object 6 however has pronounced irregularities, more particularly brighter and darker regions, which are denoted by the reference signs 21-23 in an exemplary fashion in FIG. 2. These irregularities result from the imprecise radiation attenuation assumed for the local coils in the preliminary μ-map. The iterative method described below is used to correct these irregularities and hence calibrate the μ-map of the local coils.

To this end, a difference image ΔI is first of all determined in step 48 from the image data $I_A$ and $I_B$:

$$\Delta I = I_A - I_B.$$

Furthermore, so-called attenuation correction factors (ACF) are calculated from the preliminary μ-map in step 51 for projections through the local coils 7. By way of example, this can be carried out with the aid of a Radon transform, a so-called forward projection, because the attenuation correction factor is the exponent of the forward-projected μ-map. The difference image ΔI highlights the local over- and under-corrections. By way of example, over-corrections have a value less than zero, whereas under-corrections have a value greater than zero. These differences are likewise forward-projected in step 53, and hence the differences of the logarithmic attenuation correction factors Δ log(ACF) are determined. These differences are added to the attenuation correction factors that were determined in step 51 from the preliminary radiation attenuation in order to obtain improved attenuation correction factors ACF*:

$$ACF^* := \exp(\log(ACF) + \Delta \log(ACF)).$$

Improved radiation attenuation (μ-map) of the local coils 7 is determined in step 54 by applying a back projection to the logarithm of the improved attenuation correction factors ACF*. The back projection may be a filtered or unfiltered back projection. The method is then continued in step 47, wherein the already improved radiation attenuation is now used in the subsequent iteration steps instead of the preliminary radiation attenuation. Hence, image data IB is determined in step 47 from the raw scanning data SB whilst using the improved μ-map. A difference image ΔI is determined in turn in step 48 from IA and IB. The deviations or irregularities within the difference image Δ1 are now examined in step 49. The method is completed in step 50 when the deviations are sufficiently small, that is to say when the image 20 in FIG. 2 approximates the image 30 in FIG. 3 to a sufficient extent.

Otherwise, the method is carried out further with step 51 and the above-described subsequent steps until sufficiently accurate radiation attenuation (μ-map) for the local coils 7 has been determined.

It is also possible to use other abort criteria for the method in step 49; by way of example, it is possible to determine the extent of the change in the μ-map between the last two iteration steps in step 49. The method is aborted if the change in the μ-map between the last two iteration steps is sufficiently small. Alternatively, use can also be made of thresholds for changes in the μ-map or for maximal deviations in the difference image ΔI in order to abort the method 40 when these thresholds are undershot.

Although a embodiment of the invention was described in the preceding description for determining a μ-map of local coils 7 in the MR-PET hybrid system, embodiments of the invention is not restricted thereto. Alternatively, the above-described method 40 can also be used to determine a μ-map for any other objects that are arranged in the tomography scanner 2 during a PET examination.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE SIGNS

1 MR-PET hybrid system
2 MR-PET tomography scanner
3 Object table
4 Control unit
5 Image-calculation unit
20 Image
21-23 Irregular regions
30 Image
40 Method
41-54 Step

What is claimed is:

1. A method for determining radiation attenuation as a result of a non-phantom object in a positron emission tomography scanner, the method comprising:
arranging a phantom object, which includes a positron emission source, in the positron emission tomography scanner;
acquiring first raw radiation data of the phantom object with the aid of the positron emission tomography scanner while the non-phantom object is not arranged in the positron emission tomography scanner;
calculating a first image of the phantom object from the first raw radiation data;
arranging the non-phantom object in the positron emission tomography scanner and identifying preliminary radiation attenuation by the non-phantom object arranged in the positron emission tomography scanner;

acquiring second raw radiation data of the phantom object with the aid of the positron emission tomography scanner while the non-phantom object is arranged in the positron emission tomography scanner;

calculating a second image of the phantom object from the second raw radiation data, taking into account the preliminary radiation attenuation; and determining radiation attenuation of the non-phantom object on the basis of the first image and the second image.

2. The method as claimed in claim 1, wherein the determining of the radiation attenuation comprises:

forming a difference image from the first image and the second image, determining an attenuation correction factor for a projection through the non-phantom object on the basis of the preliminary radiation attenuation, determining a modification value for the attenuation correction factor on the basis of the difference image, modifying the attenuation correction factor on the basis of the modification value, and determining the radiation attenuation on the basis of the modified attenuation correction factor.

3. The method as claimed in claim 2, wherein the determining of the modification value comprises determining a logarithmic modification value for the attenuation correction factor for the projection through the non-phantom object by a forward projection of the difference image.

4. The method as claimed in claim 3, wherein the modifying of the attenuation correction factor comprises adding the logarithmic modification value to a logarithm of the attenuation correction factor.

5. The method as claimed in claim 4, wherein the determining of the radiation attenuation comprises a back-projection of the modified attenuation correction factor for the projection through the non-phantom object.

6. The method as claimed in claim 1, wherein the calculating of a second image of the phantom object and the determining of the radiation attenuation are carried out iteratively, wherein the determined radiation attenuation of one iteration is used as preliminary radiation attenuation in the subsequent iteration.

7. The method as claimed in claim 6, wherein the iteration is finished when a difference image, made of the first image and the second image, only includes deviations below a threshold.

8. The method as claimed in claim 1, wherein the identifying of the preliminary radiation attenuation of the non-phantom object arranged in the positron emission tomography scanner comprises at least one of:

scanning the non-phantom object in a computed tomography scanner and converting measured transmission values to attenuation at 511 keV, scanning the non-phantom object in the positron emission tomography scanner with an emission source, and determining the preliminary radiation attenuation from the geometry, dimensions, and physical attenuation coefficients of the non-phantom object.

9. The method as claimed in claim 1, wherein the non-phantom object comprises a local coil of a magnetic resonance system.

10. A device for a positron emission tomography system for determining radiation attenuation as a result of a non-phantom object in a positron emission tomography scanner of the positron emission tomography system, the device comprising:

a control unit to actuate a positron emission detector of the positron emission tomography scanner; and an image-calculation unit to receive raw radiation data acquired by the positron emission detector and to reconstruct image data from the raw radiation data, wherein the device is configured to acquire first raw radiation data of a phantom object, which includes a positron emission source, arranged in the positron emission tomography scanner, while the non-phantom object is not arranged in the positron emission tomography scanner, to calculate a first image of the phantom object from the first raw radiation data, to identify preliminary radiation attenuation of the non-phantom object arranged in the positron emission tomography scanner, to acquire second raw radiation data of the phantom object while the non-phantom object is arranged in the positron emission tomography scanner, to calculate a second image of the phantom object from the second raw radiation data taking into account the preliminary radiation attenuation, and to determine the radiation attenuation on the basis of the first image and the second image.

11. The device as claimed in claim 10, wherein the positron emission tomography system comprises a combined magnetic resonance and positron emission tomography system, and wherein the non-phantom object comprises a local coil.

12. An MR-PET hybrid system with a device as claimed in claim 10.

13. A non-transitory computer program product, loadable directly into a storage medium of a programmable control unit of a device for a positron emission tomography system, including program segments to carry out the method as claimed in claim 1 when the program is executed in the programmable control unit.

14. A non-transitory electronically readable data medium including electronically readable control information stored thereon, embodied such that it executes the method as claimed in claim 1 when the data medium is used in a control unit of a device for a positron emission tomography system.

15. The method as claimed in claim 2, wherein the calculating of a second image of the phantom object and the determining of the radiation attenuation are carried out iteratively, wherein the determined radiation attenuation of one iteration is used as preliminary radiation attenuation in the subsequent iteration.

16. The method as claimed in claim 15, wherein the iteration is finished when a difference image, made of the first image and the second image, only includes deviations below a threshold.

17. The method as claimed in claim 2, wherein the identifying of the preliminary radiation attenuation of the non-phantom object arranged in the positron emission tomography scanner comprises at least one of:

scanning the non-phantom object in a computed tomography scanner and converting measured transmission values to attenuation at 511 keV, scanning the non-phantom object in the positron emission tomography scanner with an emission source, and determining the preliminary radiation attenuation from the geometry, dimensions, and physical attenuation coefficients of the non-phantom object.

18. The method as claimed in claim 2, wherein the non-phantom object comprises a local coil of a magnetic resonance system.

19. A non-transitory tangible computer readable medium including program segments for, when executed on a computer device, causing the computer device to implement the method of claim 1.

* * * * *